(12) United States Patent
Dodds et al.

(10) Patent No.: US 7,592,025 B2
(45) Date of Patent: Sep. 22, 2009

(54) VEHICLES FOR ORAL CARE WITH MAGNOLIA BARK EXTRACT

(75) Inventors: Michael W. J. Dodds, LaGrange Park, IL (US); James Roy Maxwell, Chicago, IL (US); Michael J. Greenberg, Northbrook, IL (US); Minmin Tian, Naperville, IL (US)

(73) Assignee: GIC Innovations Company, Chicago, IL (US)

( * ) Notice: Subject to any disclaimer, the term of this patent is extended or adjusted under 35 U.S.C. 154(b) by 2 days.

(21) Appl. No.: 11/602,165

(22) Filed: Nov. 17, 2006

(65) Prior Publication Data

US 2007/0134171 A1 Jun. 14, 2007

Related U.S. Application Data

(60) Provisional application No. 60/742,363, filed on Dec. 2, 2005.

(51) Int. Cl.
*A61K 36/00* (2006.01)
(52) U.S. Cl. .................................................. 424/775
(58) Field of Classification Search ........................ None
See application file for complete search history.

(56) References Cited

U.S. PATENT DOCUMENTS

| | | | |
|---|---|---|---|
| 4,547,361 A | 10/1985 | Steltenkamp et al. | |
| 4,820,544 A | 4/1989 | Barcelon et al. | |
| 5,939,050 A | 8/1999 | Lyer et al. | |
| 5,948,430 A | 9/1999 | Zerbe et al. | |
| 6,248,309 B1 | 6/2001 | Lyer et al. | |
| 6,280,751 B1 | 8/2001 | Fletcher et al. | |
| 6,284,264 B1 | 9/2001 | Zerbe et al. | |
| 6,495,512 B1 | 12/2002 | White et al. | |
| 6,500,409 B1 | 12/2002 | Scheri et al. | |
| 6,582,735 B2 | 6/2003 | Stogniew et al. | |
| 6,703,000 B2 | 3/2004 | Ning et al. | |
| 6,719,962 B2 | 4/2004 | Day et al. | |
| 6,726,897 B2 | 4/2004 | Lawlor et al. | |
| 7,025,983 B2 | 4/2006 | Leung et al. | |
| 2002/0131990 A1 | 9/2002 | Barkalow et al. | |
| 2004/0081713 A1* | 4/2004 | Maxwell et al. | 424/769 |
| 2005/0008690 A1 | 1/2005 | Miller | |
| 2006/0013779 A1* | 1/2006 | Dodds et al. | 424/58 |

FOREIGN PATENT DOCUMENTS

| | | |
|---|---|---|
| CN | 1094895 A | 11/1994 |
| CN | 1096694 | 12/1994 |
| CN | 1096695 | 12/1994 |
| CN | 1096699 | 12/1994 |
| CN | 1115212 | 1/1996 |
| CN | 94116766.6 | 1/1996 |
| CN | 1141194 A | 1/1997 |
| CN | 1073410 C | 10/2001 |
| GB | 1311060 | 3/1973 |
| JP | 84-175422 | 10/1984 |
| KR | 2002-0003413 | 1/2002 |
| WO | WO 97/35599 | 10/1997 |
| WO | WO 99/51093 | 10/1999 |
| WO | WO 01/82922 A1 | 11/2001 |
| WO | WO 0185116 A * | 11/2001 |
| WO | WO 02/072114 A2 | 9/2002 |
| WO | WO 02/091848 A1 | 11/2002 |
| WO | WO 04/000235 | 12/2003 |

OTHER PUBLICATIONS

Chang B. et al., 1998, *Planta Medica* 64: 367-369.
Rickard A.H. et al., 2003, *Trends in Microbiology* 11: 94-100.
Schreiner H.C. et al., 2003, *PNAS* 100: 7295-7300.
Sharma A. et al., 2005, *Oral Microbiology and Immunology* 20:39-42.

* cited by examiner

*Primary Examiner*—Christopher R. Tate
*Assistant Examiner*—Deborah A. Davis
(74) *Attorney, Agent, or Firm*—Brinks Hofer Gilson & Lione

(57) ABSTRACT

A vehicle and a method for oral care that includes Magnolia Bark Extract in combination with a surface active agent. The effectiveness of Magnolia Bark Extract in inhibiting biofilm formation in the oral cavity is increased by a synergistic combination of the Magnolia Bark Extract with a surface active agent in an oral cavity delivery agent, such as spray, mouthwash, toothpaste, dental cleaner, gel, dental floss, toothpick, dentifrice, and a denture cleaner.

11 Claims, No Drawings

VEHICLES FOR ORAL CARE WITH MAGNOLIA BARK EXTRACT

RELATED U.S. APPLICATION

This application claims priority to U.S. provisional patent application Ser. No. 60/742,363, filed Dec. 2, 2005.

TECHNICAL FIELD

The present invention relates, in general, to oral hygiene products compositions and, more particularly, to oral hygiene products compositions containing Magnolia Bark Extract for oral care, and to methods of making and using the oral hygiene products.

BACKGROUND

Oral hygiene (care) products have been in use for centuries. The most common of these products, toothpaste, typically consists of a mild abrasive dispersed in a gel or paste base, with detergents added to aid in cleaning, and fluoride added to reduce tooth decay. Although oral hygiene products presently on the market adequately address the need for cleaning the teeth and administering fluoride, not all existing products in the marketplace take full advantage of the ability of such a product to deliver to the oral cavity such remedies as would most benefit those individuals suffering from gum disease and tooth decay.

There is considerable consumer demand for products that freshen breath and kill bacteria in the mouth. An oral product with breath freshening and bactericidal benefits is a convenient delivery for oral cleansing in the oral cavity and freshening breath. Bacteria in the oral cavity, particularly on the tongue, can generate volatile sulfur compounds, which are a major cause of bad breath (halitosis). Of course, breath freshening is a very important part of everyday life.

In order to facilitate proper oral hygiene, oral cleansing and breath freshening practices should be conducted repeatedly throughout the day. However, oral cleansing and breath freshening may be difficult or inconvenient at times, depending on the nature of the breath freshening desired and the situation in which the breath freshening must occur. Brushing, flossing, cleaning the tongue and gargling using a variety of devices and compositions are common oral care practices well-suited for the privacy of one's home. However, such devices and compositions are less convenient to use away from the home where bathroom facilities might be scarce, unavailable or unsanitary.

Dental plaque is a microbial deposit that forms on teeth within a short time of brushing. It has been described by researchers as a soft, concentrated mass consisting mainly of a large variety of bacteria together with a certain amount of cellular debris which develops within a short time of refraining from tooth brushing. Dental plaque is not removed by rinsing with water. Dental plaque has been described as a diverse community of micro-organisms found on the tooth surface as a biofilm. The biofilm is embedded in an extracellular matrix of polymers that originate from both the tooth surface and the microbial organisms. It is generally recognized that a reduction in dental plaque promotes clean teeth, fresh breath, and healthy gums. The dental plaque biofilm, however, is very resistant to antimicrobial agents.

A reduction of the bacterial activity in the oral cavity is most important, as this activity is a major cause of most problems related to oral hygienic conditions. Antimicrobials agents that have been shown to have definite plaque-reducing abilities include chlorhexidine, cetylpyridinium chloride (CPC), Triclosan and Delmopinol. These are all medicinal and non-natural agents. Essential oils such as thymol, Eucalyptol, methyl salicylate, and menthol along with other essential oils in an alcohol-based vehicle have also been found to reduce plaque. While thymol is most effective in reducing plaque, it has a disagreeable taste. Generally, these oils benefit from the presence of an alcohol to facilitate their solubility and penetration of the plaque biofilm. While suitable for oral treatments, such as mouthwashes, high concentrations of alcohols can leave a bitter aftertaste in oral compositions, such as gums, edible films, and confectioneries, and the like.

People who wear dentures have always had a problem cleaning the same. The accepted method of doing this is to place the dentures overnight in a container with a specially formulated cleansing solution which loosens plaque and food particles so that the same can be washed away when the dentures are removed from the container and rinsed prior to further use. After eating, when extended soaking is not possible, the artificial dentures can be removed, brushed and placed back in the mouth of the user but this a laborious job and one that most artificial denture users do not relish the thought of.

Accordingly, the need exists for an active ingredient, or a combination of active ingredients, that can provide the benefits of either removing plaque, preventing or slowing down plaque formation, denture cleaning, or having an anti-inflammatory effect that would help maintain the healthy state of the gums, thereby promoting healthy gums and fresh breath. It is known to incorporate active agents into oral hygiene products for the purpose of providing oral benefits including breath freshening and bactericidal properties. Such systems have the advantage of providing rapid, effect, and convenient delivery.

BRIEF SUMMARY

The present invention is directed towards oral hygiene (care) products containing an antimicrobial agent based on Magnolia Bark Extract and a surface active agent, as disclosed herein. The antimicrobial agent can be used in different vehicles for oral care that include, but are not limited to, oral spray, mouthwash, toothpaste, dental cleaner, floss, toothpicks, dentifrices, dental pastes, and denture cleaners.

It should be understood that the present invention relates not only to methods for delivering the present oral hygiene products to the oral cavity of a human, but also to methods of delivering these compositions to the oral cavity of other animals, for example household pets or other domestic animals, or animals kept in captivity. For example, a method of use may include a person brushing a cat's teeth with one of the oral hygiene products. Another example would include the rinsing of a dog's mouth with an oral hygiene product for a sufficient amount of time to see a benefit. Pet care products such as chews and toys may be formulated to contain the active ingredients of the oral hygiene products. For example, Magnolia Bark Extract and surface active agent in combination with silica abrasive agent may be incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated active elements are released into the animal's oral cavity into a salivary medium, comparable to an effective brushing or rinsing.

In accordance with the present invention it has been unexpectedly discovered that Magnolia Bark Extract in combination with certain surface active agents is synergistically effective in inhibiting the growth of plaque-causing bacteria. The combination of Magnolia Bark Extract and selected surface active agents shows enhanced antiplaque growth activity in excess of either Magnolia Bark Extract or the surface active agent alone.

The present invention further relates to oral hygiene products containing Magnolia Bark Extract in combination with a surface active agent intended for bactericidal and breath freshening properties. More specifically, the present invention relates to an oral cavity delivery agent, such as oral spray, toothpaste, mouthwash, dental cleaner, floss, toothpicks, dentifrices, dental pastes, and denture cleaners, or other oral hygiene product containing an effective amount of Magnolia Bark Extract in combination with a surface active agent, by which the inventive composition effectively inactivates or kills oral bacteria and freshens breath through the consumption of the oral hygiene product. The surface active agent is added to the oral hygiene product to synergistically increase the effectiveness of the Magnolia Bark Extract.

In one aspect of the invention a dentifrice would be made by preparing an effective amount of the Magnolia Bark Extract in combination with a surface active agent in a conventional powder or paste carrier, the carrier being comprised of ingredients including, but not limited to, hydrophilic base, emulsifiers, flavoring agents, fragrance agents, and preservatives, in conventional proportions. Such a dentifrice may include effective amounts of abrasive components for mechanical disruption/removal of tartar and/or fluoride. A specific example of toothpaste includes an effective amount of an antimicrobial agent comprising a synergistic ratio of Magnolia Bark Extract and surface active agent, wherein the synergistic ratio is at least about 1 part Magnolia Bark Extract to 1 part surface active agent. Such antimicrobial agent is present in an amount of between about 0.2% and about 5% by weight in combination with toothpaste constituents.

Suitable surface active agents include salts of potassium, ammonium, or sodium. Sodium salts include anionic surfactants, such as alkyl sulfates, including sodium lauryl sulfate, sodium laureth sulfate, and the like. Other sodium salts include sodium lauroyl sarcosinate, sodium brasslate, and the like. Suitable ammonium salts include ammonium lauryl sulfate, ammonium laureth sulfate, ammonium lauroyl sarcosinate, ammonium brasslate, ammonium cocamidopropyl betaine, and the like. Other suitable surface active agents include emulsifiers, which can be fatty acids (for example, stearic, palmitic, oleic, and linoleic acids), their salts, glycerol monostearate, glycerol triacetate, lecithin, mono and triglycerides, and acetylated monoglycerides. As will be described below, several suitable surface active agents also show some bactericidal (germ-kill) properties on their own.

In another aspect of the invention, the oral hygiene product is produced, including but not limited to, oral spray, mouthwash, dental cleaner, floss, toothpicks, dentifrices, dental pastes, and denture cleaners. An oral care product for freshening the breath of consumers comprises water soluble portion, water insoluble portion, and an effective amount of an antimicrobial agent comprising a synergistic ratio of Magnolia Bark Extract and surface active agent. The synergistic ratio is at least about 1 part Magnolia Bark Extract to 1 part surface active agent.

In a further aspect of the invention, a method of maintaining oral hygiene includes applying an oral care product to the oral cavity, where the oral care product includes an effective amount of an antimicrobial agent. The antimicrobial agent comprises a synergistic ratio of Magnolia Bark Extract and surface active agent, wherein the synergistic ratio is at least about 1 part Magnolia Bark Extract to 1 part surface active agent.

DETAILED DESCRIPTION

It is known to use oral care products as a vehicle for delivering components to the oral cavity for providing oral benefits such as breath freshening and bactericidal properties. Such systems have the advantage of providing a consumer with a convenient and inexpensive method for maintaining oral health and fresh breath throughout the course of the day.

The present invention is directed to oral hygiene (care) products that have antimicrobial properties. The oral hygiene products comprise Magnolia Bark Extract and a surface active agent. The invention is further directed to a method of reducing or eliminating microorganisms present in the oral cavity, comprising absorbing in the oral cavity an oral care product comprising Magnolia Bark Extract and a surface active agent. As well, the invention is directed to a process for preparing the oral hygiene products.

Suitable oral hygiene (care) products for humans include, but are not limited to, oral spray, mouthwash, toothpaste, dental cleaner, floss, toothpicks, dentifrices, dental pastes, tongue scrubbers, and denture cleaners that contain Magnolia Bark Extract and a surface active agent according to the present invention. Suitable oral hygiene (care) products for animals include, but are not limited to, oral spray, mouthwash, toothpaste, dental cleaner, floss, toothpicks, dentifrices, dental pastes, denture cleaners, edible films, tongue scrubbers and chewable toys that contain Magnolia Bark Extract and a surface active agent according to the present invention.

In one aspect of the invention, a particular formulation of compounds is provided, including not only the more commonly used vitamins and minerals, but also including beneficial herbal ingredients, as well other medicinal ingredients that act together to reduce and prevent major chronic diseases of the mouth. Such a formulation is provided in a form directly absorbable through the mouth, without need of assimilation through the digestive system.

In one aspect of the invention, this formulation is combined into carriers in common use, such as toothpaste or mouthwash, so that individuals can gain the advantage of use without the need for taking a pill. In another aspect of the invention, this formulation may be combined into carriers commonly used in the environment of the dental office, carriers such as dental prophylaxis paste, oral subgingival irrigation fluid, or biologically absorbable or nonresorbable fiber matrices, so that the benefits of these remedies can become part of the existing armamentarium of dentists and dental hygienists.

A "dentifrice" is defined as an oral care product that is to be used in conjunction with a toothbrush to clean the accessible tooth surfaces, tongue, and the oral cavity.

The term "absorbing" includes operations by which an oral care product is wholly or partially consumed while it is being held in the mouth, such as by prolonged rinsing, chewing, sucking, or dissolving. Holding the product in the mouth for longer periods of time is expected to be associated with greater reduction of the microorganisms present in the oral cavity. Suitably effective periods of time for absorbing the oral care products range from 3-5 minutes, up to 20-30 minutes, and will vary with the type of oral care product.

The carrier for the components of the present compositions can be any orally-acceptable vehicle suitable for use in the oral cavity. Such carriers include the usual components of oral sprays, mouthwashes, toothpastes, tooth powders, dental pastes, solid and liquid dentifrices and the like, and are more fully described hereinafter.

The present invention incorporates Magnolia Bark Extract as the active component for oral bactericidal benefits. Magnolia Bark Extract is known to have bactericidal and antifungal properties. For example, magnolol and honokiol are two components in Magnolia Bark Extract with known antimicrobial activity.

The Magnolia Bark Extract used in the present invention may be obtained from O' Laughlin Industries, Co. LTD, Guang Zhou Masson Pharmaceutical Co., or Honsea Sunshine Bioscience and Technology Co. The Magnolia Bark Extract is obtained in the form of powder. The Magnolia Bark Extract is dissolved with the flavor and may be warmed to dissolve prior to making the oral product. Magnolia Bark Extract can be formulated using standard formulation techniques into a variety of oral care products.

While it is relatively easy to kill bacteria in solutions, the plaque biofilm is a complex environment that provides protection from environmental threat to the bacteria, as well as synergies between bacterial species (Sharma A. et al., 2005, *Oral Microbiology and Immunology* 20: 39-42). Therefore, compared to a simple germ kill test, it is much harder to show actual efficacy against established plaque by an antimicrobial agent. Diffusion into the biofilm is limited, and bacteria within the bulk of the biofilm are protected from exposure to the agent by extracellular material, such as the glucan and dextran polysaccharides. It is, therefore, arguably easier to prevent formation of plaque than it is to remove an established plaque.

In accordance with the present invention, the antimicrobial effects of Magnolia Bark Extract are enhanced through the combination of Magnolia Bark Extract with a surface active agent. Although not intending that the invention be limited to any particular theory, it is believed that the combination of a surface active agent with an effective amount Magnolia Bark Extract can provide an oral care product that promotes the reduction of biofilms in dental plaques and in other areas of the oral cavity, such as the tongue. It is believed that the combination of Magnolia Bark Extract and a suitable surface active agent may prevent bacterial attachment to the acquired pellicle. Such an oral care product may slow down or prevent plaque accumulation. Further, the oral care product of the invention can be effective in the removal of existing plaque in combination with enzymes, additional surface active agents, abrasives or combinations thereof.

A preferred surface active agent is one that increases the solubility of Magnolia Bark Extract and that can be used as a food additive. Suitable surface active agents include but are not limited to common surfactants, soaps, wetting agents, and emulsifiers. Some examples of surfactants include but are not limited to salts of potassium, ammonium, or sodium. Sodium salts include anionic surfactants, such as such as alkyl sulfates, including sodium lauryl sulfate, sodium laureth sulfate, and the like. Other sodium salts include sodium lauroyl sarcosinate, sodium brasslate, and the like. Suitable ammonium salts include ammonium lauryl sulfate, ammonium laureth sulfate, ammonium lauroyl sarcosinate, ammonium brasslate, ammonium cocamidopropyl betaine, and the like. Other suitable surface active agents include emulsifiers, which can be fatty acids (for example, stearic, palmitic, oleic, and linoleic acids), their salts, glycerol monostearate, glycerol triacetate, lecithin, mono and triglycerides, and acetylated monoglycerides. As will be described below, several suitable surface active agents also show some bactericidal (germ-kill) properties on their own.

The oral hygiene product of this invention can also include additional breath freshening or oral health ingredients, which can be antimicrobial in nature. Further, the additional breath freshening or oral health ingredients can comprise food acceptable salts of zinc or copper, cooling agents, pyrophosphates or polyphosphates, and the like.

The invention also includes a treatment method for reducing the number or activity of bacteria in the oral cavity of a consumer, providing an oral care product comprising Magnolia Bark Extract in combination with a surface active agent in an amount sufficient to kill or deactivate oral bacteria. The person in need of the treatment consumes the oral care product whereby the bacteria in the oral cavity of the person are reduced or inactivated by the treatment.

In one form, the oral care product is formulated with an oral cavity, delivery agent to deliver at least about 0.001% to about 2.0% concentration of Magnolia Bark Extract to the oral cavity. In another form, the oral care product is formulated with an oral cavity delivery agent to deliver at least about 0.01% concentration of Magnolia Bark Extract to the oral cavity. One or more surface active agents are added to the oral care product so as to enhance the effectiveness of the oral care product in the delivery of an effective amount to the oral cavity.

In accordance with one embodiment of the invention, one or more surface active agents are present in the oral care product in a concentration range of about 0.001% to about 2.0%. In the oral care product, Magnolia Bark Extract is combined with a surface active agent in a synergistic ratio that provides enhanced germ-kill effectiveness. The synergistic ratio ranges from about 1 part Magnolia Bark Extract to 1 part surface active agent up to about 4 parts Magnolia Bark Extract to 1 part surface active agent. One particularly effective surface active agent is sodium lauryl sulfate, and a particularly effective synergistic composition is about 2 parts Magnolia Bark Extract to 1 part sodium lauryl sulfate.

Given that Magnolia Bark Extract is a hydrophobic compound, there are several oral cavity delivery agents that may be used to enhance the release of the Magnolia Bark Extract from the oral care product. For example, in a dentifrice such as toothpaste, the formulation includes a paste base that is hydrophobic, which also inhibits the release of the Magnolia Bark Extract. In the various embodiments of the inventive oral care composition, the Magnolia Bark Extract is combined with a surface active agent and may be encapsulated, spray dried, or formulated into a coating, or combinations thereof in order to facilitate and speed the release of the Magnolia Bark Extract into the oral cavity.

To evaluate the effectiveness of Magnolia Bark Extract, in vitro tests were conducted with three subgingival plaque bacteria associated with oral malodor. The Minimum-Inhibitory-Concentrations (MIC) study protocol is as follows. Chlorhexidine was used as a positive control and sterile water was used as a negative control. Menthol and Tween 80 was used as a solvent for Magnolia Bark Extract. Tween 80 is the common name for Polysorbate 80. Ninety-six-well microtiter plates were used for this study. Each well contained $5 \times 10^5$ colony forming units/ml of bacteria, serially diluted agents and bacterial growth medium. All bacterial cultures were incubated at 37° C. and stationary. Bacterial growth was estimated spectrophotometrically at 660 nm, after 48 hours. The MIC for each test bacteria was defined as the minimum concentration of test compound limiting turbidity to less than 0.05 absorbance measured at 660 nm.

The Minimum-Bactericidal-Concentrations (MBC) were determined using the 96-well microtiter plate serial dilutions as described above for MIC studies. Serial dilutions of cultures in wells showing no visible growth were performed and 10 microliters of culture were plated in triplicate on blood agar plates. Viable colonies were scored after incubation of the plates for 48 hours at 37° C. For each test bacterium, the number of colony forming units/ml (CFU/ml) was determined in the initial inoculum. The MBC was defined as the lowest concentration of a test compound that killed at least 99.9% of the cells present in the initial inoculum.

The results of the studies performed to obtain MIC and MBC of Magnolia Bark Extract (MBE) are as follows. Against *Streptococcus mutans* a Magnolia Bark Extract of 90% had an MIC of 15.62 µg/ml. For *Porphyromonas gingivalis*, the 90% Magnolia Bark Extract had an MIC of 3.91 µg/ml, and the 65% Magnolia Bark Extract had an MIC of 7.82 µg/ml. For *Fusobacterium nucleatum* the 90% Magnolia Bark Extract had an MIC of 3.91 µg/ml and an MBC of 7.82 µg/ml. Against the same organism, the 65% Magnolia Bark Extract had an MIC and MBC of 7.82 µg/ml. Chlorhexidine was the positive control and produced an MIC and MBC of 1.25 µg/ml for all three bacteria. The solvent consisting of water with 10% methanol and 3.8% Tween 80 had no noticeable growth inhibitory effects on any of the three bacteria in the study.

It is also known that Magnolia Bark Extract is effective against *Actinobacillus actinomyecetemcomitans, Prevotella intermedia, Micrococcus luteus, Bacillus subtilis, Veillonella disper, Capnocytophaga gingivalis*, and periodontal microorganisms (Chang B. et al., 1998, *Planta Medica* 64: 367-369). Many of these human pathogens are associated with periodontal diseases (Schreiner H. C. et al., 2003, *PNAS* 100: 7295-7300). It is also known that many of the above-mentioned bacterial species co-aggregate to create biofilm (Rickard A. H. et al., 2003, *Trends in Microbiology* 11: 94-100).

Further to the results described above, the effect of Magnolia Bark Extract on biofilm formation and removal was compared with different herbal and natural ingredients. Comparative testing was performed using green tea extract, Oolong tea extract, Licorice, and Magnolia Bark Extract. The comparative testing included determining the solubility in water, ethanol, water:ethanol mixtures and other solvents (for example, Tween in water), MIC for growth of *S. mutans*, MIC for formation of *S. mutans* biofilm in 96-well plates, and the effect on detachment of *S. mutans* biofilm.

The green tea was soluble in water; all other substances were found to be soluble in a 2:1 water:ethanol mixture. Magnolia Bark Extract was also soluble in 0.01 µl of 50% Tween 80 in water.

To evaluate the effect on *Streptococcus mutans* biofilm formation, 96-well microtiter plates were used. Each well contained *S. mutans* ($5\times10^6$ CFU/ml), and was serially diluted with test compounds and growth medium (brain heart infusion broth (BHI) with 0.5% sucrose). The controls included inoculated growth medium without test compounds. All plates were incubated at 37° C. under aerobic condition with growth estimated spectrophotometrically (660 nm) after 48 h using a microtiter plate reader. Then, the supernatant containing unattached cells was removed from each wells by aspiration, the attached biofilm mass was dissolved with 200 µl 1 N NaOH and the optical density was measured at 660 nm using the microtiter plate reader. Chlorhexidine (40 µg/ml) was used as a positive control.

To further evaluate the effect on *S. mutans* biofilm detachment, sterile 96-well microtiter plates were used where each well was inoculated with *S. mutans* ($5\times10^6$ CFU/ml), growth medium (BHI supplemented with 0.5% sucrose), and incubated at 37° C. under aerobic condition for biofilm formation. After 48 hours, the non-attached supernatant was aspirated and serially diluted. Test compounds were added to the pre-formed biofilm and incubated at 37° C. under aerobic condition. The controls included solvent without test compounds. After 30 min, the supernatant was aspirated from wells and the biofilm remaining after treatment was dissolved in 200 µl 1N NaOH, and quantitated at 660 nm using the plate reader. A chlorhexidine positive control was used. If detachment of the biofilm by action of the test compounds occurred, the spectrophotometric absorbance or optical density (OD) should show a decrease compared to the non-treated control.

The results of the comparative testing are show below in Table 1. The test results are presented in units of µg/ml for each of the compounds. In Table 1, and in the following Tables, Magnolia Bark Extract is designated as "MBE" and the chlorhexidine positive control is designated as "CHX."

TABLE 1

Comparative Effect on MIC and Biofilm (µg/ml)

| Test | Green tea | Oolong tea | Licorice | MBE | CHX |
|---|---|---|---|---|---|
| MIC growth | 250 | 1000 | 250 | 7.8 | 2.5 |
| MIC biofilm formation | 250 | 250 | 250 | 7.8 | 2.5 |
| MIC biofilm detachment | >1000 | >1000 | >10000 | >1000 | >10 |

The data shown in Table 1 indicates that none of the compounds tested were more effective than chlorhexidine at removing the established biofilm. The green tea extract, licorice extract and Magnolia Bark Extract may inhibit *S. mutans* biofilm by inhibiting bacterial growth, since MICs are identical for both growth and biofilm formation. The Oolong tea did not inhibit planktonic growth, but was more effective at inhibiting the biofilm. Magnolia Bark Extract was most effective at inhibition of both growth and biofilm formation and well within an order of magnitude of the chlorhexidine positive control.

Although useful to show the comparative effect of Magnolia Bark Extract on biofilm formation and MIC growth, the foregoing test procedure may not effectively mimic the in vivo exposure of an oral care product to a developing plaque biofilm. In an in vivo situation, the active could be exposed to the plaque for a defined period of time at a set frequency (for example, for 5 minutes, three times a day). Therefore, a series of comparative experiments were conducted to mimic the in vivo use of potential active ingredients. To perform the tests the saliva compositions listed below in Tables 2 and 3 were prepared.

TABLE 2

Saliva buffer composition
(filter sterilize after preparation)

| Compound | mg/L |
|---|---|
| Ammonium chloride | 233 |
| Calcium chloride, dihydrate | 210 |
| Magnesium chloride, hexahydrate | 43 |
| Potassium chloride | 1162 |
| $KH_2PO_4$ (monobasic potassium phosphate) | 354 |
| Potassium thiocyanate | 222 |
| Sodium citrate | 13 |
| Sodium bicarbonate | 535 |
| Dibasic sodium phosphate, $Na_2HPO_4$ | 375 |
| Urea | 173 |

TABLE 3

Supplemented Saliva Medium
(filter sterilize after preparation)

| Ingredient | wt. % |
|---|---|
| Whole saliva | 25 |
| Saliva buffer | 45 |
| Modified eagle medium (MEM) | 20 |
| Trypticase soy broth | 10 |

A mixed culture system that utilizes the bacteria from freshly-collected stimulated whole saliva was used. Saliva cell pellets were used to inoculate saliva-coated hydroxyapatite (S-HA) discs. The discs were placed in 24-well cell culture plates and incubated for up to 3 days. Biofilms were exposed to actives on days 2 and 3 (starting at 18 hours), and quantified on day 4. The number of bacteria was determined by spectrophotometric absorbance or optical density (OD) at 600 nm. The five phases of the experiment were: pellicle formation; bacterial attachment; biofilm growth; exposure to actives; and bacterial enumeration.

To form the pellicles, HA Discs were ultrasonically washed in deionized water and air-dried, then autoclaved. The discs were placed in a 24-well plate with 1 ml 50% sterile saliva (1 part sterile whole saliva: 1 part saliva buffer, filter sterilize after preparation) for 2 hours on slow agitation at room temperature. The saliva was suctioned and then the discs were transferred to fresh wells for bacterial attachment.

To form the biofilms, the bacterial suspension was removed, and the discs were transferred to fresh wells. One ml of supplemented saliva medium was added and the plate was placed in the incubator for overnight incubation and for the duration of the experiment (up to 72 hours).

A stock solution of 1% Magnolia Bark Extract in 60% ethanol was prepared. Magnolia Bark Extract samples were prepared having a concentration range of 125, 250, 500, and 1000 μg/ml (ppm) in a Phosphate-Buffered-Saline (PBS) solution, where the negative control was PBS and the positive control was CHX having a concentration of 0.12%. The PBS control solution had a composition as shown below in Table 4.

TABLE 4

Phosphate Buffered Saline Composition

| Ingredient | g/L |
|---|---|
| NaCl | 8.0 |
| KCl | 0.2 |
| Na$_2$PO$_4$ | 1.44 |
| KH$_2$PO$_4$ | 0.24 |

One ml quantities of active ingredients and controls were placed into fresh wells, and the discs were transferred to these wells for 5 minutes. The chlorhexidine control exposure was one minute, two times a day to mimic the standard mouthrinse procedure. The exposure to active ingredient was carried out at 8:00 AM, 12:00 and 4:00 PM. After the timed exposure, the solution was removed and the discs washed twice with PBS and then transferred to fresh medium. For some experiments, the medium used during the day was TSB (Tryptic Soy Broth) with a 50 μl 40% sterile sucrose solution added to each well (to give a 2% sucrose solution). The medium was not replaced after the mid-day exposure.

After overnight incubation (day 2), discs were exposed to controls and actives. On day 3 the biofilms were again exposed to tests and controls. On day 4 the discs were removed from the medium, the medium pH was measured to obtain an indication of metabolic activity, and the discs were placed into tubes with 2.5 ml PBS, vortexed for 20 sec, and then placed into the ultrasonic bath for another 20 sec. The suspension was transferred into cuvettes and the bacterial cell density determined by OD measurements at 600 nm.

The results of the pH measurements are shown below in Table 5 and the percentage reductions in OD compared to PBS control are shown below in Table 6.

TABLE 5 pH Measurements

| Test Sample | pH |
|---|---|
| PBS Control | 5.4 |
| CHX Control | 8.8 |
| MBE 125 | 5.2 |
| MBE 250 | 6.0 |
| MBE 500 | 7.1 |
| MBE 1000 | 7.6 |

TABLE 6

Percentage Reductions in Optical Density at 600 nm

| Test Sample | % OD reduction |
|---|---|
| PBS Control | 0 |
| CHX Control | 84 |
| MBE 125 ppm | −2 |
| MBE 250 ppm | 21 |
| MBE 500 ppm | 53 |
| MBE 1000 ppm | 59 |

The results shown above in Tables 5 and 6 illustrate a clear effect and dose-response of Magnolia Bark Extract on inhibition of biofilm metabolic activity (as determined by pH of the medium) and biofilm formation (OD). Chlorhexidine had a strong inhibitory effect on plaque metabolism and cell number. Magnolia Bark Extract was less effective than chlorhexidine, but the chlorhexidine concentration was slightly higher than the Magnolia Bark Extract.

To evaluate the effect of Magnolia Bark Extract in combination with the surface active agent, sodium lauryl sulfate, five active ingredient solutions were prepared using the procedures described above. The chlorhexidine control solution was prepared having a slightly reduced concentration of 0.1% (1000 ppm). Also, the MBE solutions were prepared to have a concentration of 500 ppm. Sodium lauryl sulfate was added to two of the Magnolia Bark Extract solutions to obtain SLS concentrations of 0.05% and 0.1% in the Magnolia Bark Extract solutions. The testing with Magnolia Bark Extract described above was repeated with the five solutions.

The pH test results are shown below in Table 7, where sodium lauryl sulfate is designated as "SLS."

TABLE 7 pH Measurements

| Test Sample | pH |
|---|---|
| PBS Control | 4.9 |
| CHX Control | 8.8 |
| SLS 1000 ppm | 5.7 |
| MBE 500 ppm | 7.1 |
| MBE 500 ppm/SLS 500 ppm | 5.9 |
| MBE 500 ppm/SLS 1000 ppm | 6.2 |

The percentage reductions in optical density (OD) test results are shown below in Table 8. Note that the data in the last row of this table were taken from a different experiment.

TABLE 8

Percentage Reduction in Optical Density at 600 nm

| Test Sample | % OD reduction |
|---|---|
| PBS Control | 0 |
| CHX Control | 94 |
| SLS 1000 ppm | 61 |
| MBE 500 ppm | 65 |
| MBE 500 ppm/SLS 500 ppm | 79 |
| MBE 500 ppm/SLS 1000 ppm | 70 |
| MBE 1000 ppm/SLS 500 ppm | 88 |

The results listed above in Tables 7 and 8 show that the chlorhexidine control had the highest pH and this control also had the lowest OD. Based on pH data (an indication of metabolic activity), 500 ppm Magnolia Bark Extract alone was more inhibitory than the sodium lauryl sulfate or the Magnolia Bark Extract/sodium lauryl sulfate mixtures. The OD absorbance data (bacterial number), however, indicates a synergistic effect at reducing the biofilm in test solutions combining Magnolia Bark Extract and sodium lauryl sulfate. In particular, the results show that the 1000 ppm sodium lauryl sulfate and 500 ppm Magnolia Bark Extract had similar effects in terms of plaque quantity, although Magnolia Bark Extract inhibited plaque metabolic activity to a greater extent. The Magnolia Bark Extract with sodium lauryl sulfate at 500 ppm reduced plaque growth compared to 500 ppm Magnolia Bark Extract alone. Further, the sodium lauryl sulfate at 1000 ppm was less effective than at 500 ppm in combination with 500 ppm Magnolia Bark Extract. The most effective combination was 1000 ppm of Magnolia Bark Extract in combination with 500 ppm of sodium lauryl sulfate.

Although not wishing to be bound by any particular theory regarding the active mechanism of the invention, it is possible that the reason for the paradoxical effect of decreased cell mass with increased metabolic activity of the Magnolia Bark Extract/sodium lauryl sulfate mixtures relates to the action of the sodium lauryl sulfate in allowing more rapid penetration of the Magnolia Bark Extract into the biofilm, where it has an immediate germ kill and/or growth-inhibitory effect, but the Magnolia Bark Extract is also rinsed away more easily, so the substantivity and prolonged metabolic effect is minimized.

To evaluate the germ-kill efficacy and synergist effect when two or more germ-kill actives are combined, testing was performed to determine the ratio of MBE to surface active agent. The germ-kill active and/or surface active agent were dissolved in ethanol or sterile water to give an initial concentration 0.1% to 1%. The solution was diluted with a nutrient broth to give an initial concentration of 0.05% to 0.5%, which was then serially diluted two-fold so that each subsequent dilution contained 50% of the compound concentration of the previous dilution while maintaining a constant level of nutrients for each dilution. These dilutions were inoculated with representative oral microorganisms, or incubated saliva, and incubated for 24 hours at 37° C. For each surface active agent, the lowest dilution that was not turbid was registered as the MIC. The MBC was determined by transferring 10 microliter of liquid from non-turbid tubes to fresh growth media and incubated for 48 hours. For each surface active agent, the lowest dilution that did not demonstrate growth was considered the MBC.

Table 9 below shows the MIC of various surface active agents and emulsifiers on incubated saliva.

TABLE 9

Minimum-Inhibitory-Concentration of Selected Surface Active Agents

| Sample | MIC (ppm) |
|---|---|
| Sodium Lauryl Sulfate | 50 |
| Betaine BF-20 | >1000 |
| Tego Betain CKD | 25 |
| Tego Betain ZF | 25 |
| Sodium Brasslate | 500 |
| Sodium Lauroyl Sarcosinate | 100 |
| Sodium Stearoyl Lactylate | >3000 |
| Tween 20 | >1000 |
| Sucrose Stearate | >500 |
| Sucrose Distearate | >500 |
| Chlorhexidine gluconate* | 2 |

*used as a positive control

The results show that sodium lauryl sulfate and Cocamidopropyl Betaine are good germ-kill surface active agents, while sodium brasslate shows a moderate germ-kill efficacy. Sodium stearoyl lactylate, Polysorbate 20 (commonly known as Tween 20), Sucrose stearate, and Sucrose distearate are weak or non germ-kill actives.

To evaluate the synergistic effect of an active ingredient in combination with a surface active agent, the fractional inhibitory index (FIC) was computed according to equation (1) below:

$$FIC = [MIC_{A\text{-combined with }B}/MIC_{A\text{ alone}} + MIC_{B\text{-combined with }A}/MIC_{B\text{-alone}}] \tag{1}$$

where an FIC value of less than 1.0 is synergistic, an FIC between 1.0 and 2.0 is additive, and an FIC greater than 2.0 is antagonistic.

Table 10 below shows the MIC values for combinations of Magnolia Bark Extract/sodium lauryl sulfate and Magnolia Bark Extract/Tween-20 on S. mutans:

TABLE 10

Minimum-Inhibitory-Concentration of Selected Surface Active Agents

| Sample | MIC/ppm | FIC |
|---|---|---|
| Sodium Lauryl Sulfate | 100 | — |
| Magnolia Bark Extract | 25 | — |
| MBE/SLS 1/4 | 50 | 1 |
| MBE/SLS 3/2 | 25 | 0.70 |
| MBE/SLS 4/1 | 25 | 0.85 |
| MBE/Tween 20 100/100 | 25 | 1 |
| MBE/Tween 20 100/250 | >100 | >2 |
| MBE/Tween 20 100/500 | >100 | >2 |
| Chlorhexidine gluconate* | 2 | — |

The results indicate that Magnolia Bark Extract and sodium lauryl sulfate show synergistic effect (FIC <1) when combined in a ratio (MBE/SLS) between about 1/4 to about 4/1. However, Magnolia Bark Extract and Tween-20 show antagonist effect (FIC >2) when combined.

In particular, the results show that certain ratios of Magnolia Bark Extract to sodium lauryl sulfate show synergistic effects. Accordingly, the present invention contemplates oral care products that contain a synergistic ratio of Magnolia Bark Extract to a surface active agent. From the foregoing experimental results, Magnolia Bark Extract in combination with a surface active agent will produce a synergistic antimicrobial effect in an oral care product. Oral care products having a surface active agent in a concentration range of about 25 ppm to about 500 ppm in combination with Magnolia Bark Extract show synergistic properties for inhibiting the biofilm formation that leads to dental plaque. Further, oral care products having a weight ratio of at least about one part Magnolia Bark Extract to one part surface active agent will produce a synergistic antimicrobial effect in an oral care product. Further, the synergistic ratio of Magnolia Bark Extract to surface active agent can range from about 1 part Magnolia Bark Extract to 1 part surface active agent up to about 4 parts Magnolia Bark Extract to 1 part surface active agent. Most preferably, the synergistic ratio is about 2 parts Magnolia Bark Extract to 1 part surface active agent. Accordingly, the present invention contemplates a wide range of oral care products containing a synergistic combination of Magnolia Bark Extract and a surface active agent.

To evaluate the antimicrobial efficacy in an oral care product, Table 11 below lists examples of formulations of Magnolia Bark Extract in chewing gum. Example 1 is a comparative example of a prior art gum formulation.

TABLE 11

Antimicrobial Gum Formulas (dry weight percent basis)

| Ingredient | Example 1 | Example 2 | Example 3 | Example 4 | Example 5 |
| --- | --- | --- | --- | --- | --- |
| Gum Base | 25.21 | 25.21 | 25.21 | 25.21 | 25.21 |
| Lecithin | 0.17 | 0.17 | 0.17 | 0.17 | 0.17 |
| $NaHCO_3$ | 0.25 | 0.25 | 0.25 | 0.25 | 0.25 |
| Sorbitol | 50.86 | 49.86 | 47.86 | 45.86 | 50.36 |
| MBE | — | 1.00 | 3.00 | 5.00 | 0.50 |
| Mannitol | 4.25 | 4.25 | 4.25 | 4.25 | 4.25 |
| Lycasin/Glycerin | 8.51 | 8.51 | 8.51 | 8.51 | 8.51 |
| Glycerin | 8.50 | 8.50 | 8.50 | 8.50 | 8.50 |
| Encapsulated Sweetener | 0.67 | 0.67 | 0.67 | 0.67 | 0.67 |
| Flavor | 1.58 | 1.58 | 1.58 | 1.58 | 1.58 |
| Total | 100.00 | 100.00 | 100.00 | 100.00 | 100.00 |

In accordance with the invention, each of the formulations in examples 2-5 is supplemented with a surface active agent as described above. In one exemplary embodiment, each of the examples 2-5 includes about 0.01% to about 2% of a surface active agent as described above. In another exemplary embodiment, each of the examples 2-5 includes about 25 ppm to about 500 ppm of a surface active agent as described above. In yet another exemplary embodiment, each of the examples 2-5 includes sodium lauryl sulfate and Magnolia Bark Extract in a ratio of about 1/4 to about 4/1.

The present invention also provides methods of producing the oral care products. In one embodiment, the formulations suitable for oral delivery are prepared by forming a base solution that includes at least three types of edible film forming agents, such as maltodextrins, hydrocolloids and fillers and processing the base solution to form an edible film that is suitable for coating of, impregnating of, or admixing with, various oral delivery products of this invention. Typically, the base solution of such a film is prepared by adding an initial mixture of dry ingredients to water that is stirred.

Additional ingredients, such as flavor/emulsifier blends, sweeteners, softeners, color, the like or combinations thereof, can be added to the base solution. In one aspect, the solution is stirred continuously and heated at a temperature ranging from about 40° C. to about 60° C. The solution can then be dried in any suitable manner, thereby forming the edible film. It should be obvious that the drying of the edible film can take place after upon application of the film onto dental cleaners, toothpicks, dental floss, and other oral hygiene products of this invention.

It should be appreciated that any suitable type, number and arrangement of process procedures or steps (i.e., mixing, heating, drying, cooling, and addition of ingredients), process parameters (i.e., temperature, pressure, pH, process times) or the like can be utilized.

By way of example and not limitation, the following examples in Tables 12 and 13 below illustrate various embodiments of the edible film formulations of the present invention.

TABLE 12

Antimicrobial Edible Film Formulations (dry weight percent)

| Ingredient | Example 6 | Example 7 | Example 8 | Example 9 | Example 10 |
| --- | --- | --- | --- | --- | --- |
| Maltodextrin | 25.00 | 44.75 | 28.20 | 34.20 | 18.05 |
| Sodium Alginate | 21.20 | — | 19.00 | — | 12.00 |
| Calcium Alginate | — | 15.15 | — | 11.45 | — |
| Carageenan | — | — | — | — | 12.00 |
| Microcrystalline Cellulose | 25.75 | 9.00 | 18.80 | 13.00 | 20.00 |
| Calcium Carbonate | — | 2.45 | — | — | — |
| Glycerin | 12.25 | 10.00 | 8.00 | — | 9.5 |
| Sorbitol | — | — | — | 6.00 | 1.55 |
| Propylene Glycol | — | — | 3.65 | 5.00 | — |
| Menthol | 1.00 | 0.05 | — | 1.25 | — |
| Eucalyptol | — | 0.05 | — | 1.00 | — |
| Maleic Acid | — | — | — | — | 1.35 |

TABLE 12-continued

Antimicrobial Edible Film Formulations (dry weight percent)

| Ingredient | Example 6 | Example 7 | Example 8 | Example 9 | Example 10 |
|---|---|---|---|---|---|
| Citric Acid | — | — | 1.25 | — | 1.00 |
| Chlorohexidene | 1.85 | — | — | 1.00 | — |
| Triclosan | — | 1.25 | — | 1.00 | — |
| Flavor | 9.40 | 11.00 | 12.00 | 14.00 | 10.00 |
| High Intensity Sweetener | 1.50 | 1.25 | 1.00 | 1.05 | 1.45 |
| MBE | 1.00 | 3.00 | 5.00 | 8.00 | 10.00 |
| Color | 0.05 | 0.05 | 0.05 | 0.05 | 0.10 |
| Sodium laurel sulfate | 1.00 | 2.00 | 3.00 | 3.00 | 3.00 |
| Total | 100.00 | 100.00 | 100.00 | 100.00 | 100.00 |

In accordance with the invention, each of the formulations in examples 6-10 is supplemented with a surface active agent as described above. In one exemplary embodiment, each of the examples 6-10 includes about 0.01 to about 2% surface active agent.

TABLE 13

Antimicrobial Edible Film Formulations (dry weight percent basis)

| Ingredient | Example 11 | Example 12 | Example 13 | Example 14 | Example 15 |
|---|---|---|---|---|---|
| Maltodextrin | 35.00 | 30.35 | 28.15 | 25.00 | 30.00 |
| Sodium Alginate | 22.15 | 19.10 | 17.00 | 28.15 | — |
| Carageenan | — | — | — | — | 20.15 |
| Microcrystalline Cellulose | 20.00 | 18.00 | 17.00 | 17.00 | 18.00 |
| Gum Arabic | — | — | 11.00 | — | — |
| Glycerin | 7.30 | 15.00 | 7.30 | 7.30 | 7.30 |
| Flavor | 11.00 | 11.00 | 11.00 | 11.00 | 11.00 |
| Lecithin | 2.00 | 2.00 | 2.00 | 2.00 | 2.00 |
| High Intensity Sweetener | 1.50 | 1.50 | 1.50 | 1.50 | 1.50 |
| MBE | 1.00 | 3.00 | 5.00 | 8.00 | 10.0 |
| Color | 0.05 | 0.05 | 0.05 | 0.05 | 0.05 |
| Total | 100.00 | 100.00 | 100.00 | 100.00 | 100.00 |

In accordance with the invention, each of the formulations in examples 6-15 in Tables 12 and 13 is supplemented with a surface active agent as described above. In one exemplary embodiment, each of the examples 6-15 includes about 0.01 to about 2% a surface active agent as described above. In another exemplary embodiment, each of the examples 6-15 includes about 25 ppm to about 500 ppm of a surface active agent as described above. In yet another exemplary embodiment, each of the examples 6-15 includes sodium lauryl sulfate and Magnolia Bark Extract in a ratio of about 1/4 to about 4/1.

EXAMPLES

The examples listed below are not intended to exclude other variations in formulations and the present invention is not limited to these formulations.

Oral Care Compositions

The invention includes oral hygiene products containing the compounds having antimicrobial properties, as disclosed previously herein. In principle, these oral hygiene products may be solids, gels, liquids, creams, sprays (aerosols), or combinations thereof. Such oral hygiene products include, but are not limited to, dentifrices, dental pastes, oral sprays, mouthwash, toothpaste, toothpowder, dental cleaner, dental floss, toothpicks, dental pastes, denture cleaners, and other oral care products.

In principle, any relevant controlled formulation technique for preparing an oral controlled release composition may be applied. Thus, the antimicrobial active may be in the form of a liquid having particles dispersed in a dispersion medium or it may be in the form of a single or a multiple unit dosage form intended for use as such as for dispersing in a dispersion medium before use.

In a preferred embodiment of the present invention, an effective amount for antimicrobial benefit of Magnolia Bark Extract in combination with a surface active agent, such as described above, is present in an oral care formulation. In another aspect of the present invention, the amount of Magnolia Bark Extract is present in an amount up to 5% by weight of the oral care product. In yet another aspect of the present invention, the amount of Magnolia Bark Extract is 1% of the weight of the oral care product. In still another aspect, the Magnolia Bark Extract is present in the amount of 0.01% by weight of the oral care product. Considering the potency of Magnolia Bark Extract as described in the in vitro studies above, levels as low as 0.005% by weight of the oral care product should be effective in terms of bactericidal properties. The absolute amount of sodium lauryl sulfate in the oral care formulation can range from about 4 mg to about 10 mg.

In a preferred embodiment of the invention, the Magnolia Bark Extract and the surface active agent may be prepared and used in various forms applicable to the mouth such as toothpastes, toothpowders, liquid dentifrices, mouthwashes, troches, dental pastes, gingival massage creams, gargle tablets, and other formulations for the mouth to aid in the prevention and/or treatment of dental caries or tooth decay. The oral hygiene product according to this invention may further include additional well known ingredients depending on the type and form of a particular oral hygiene product.

Exemplifying solid oral hygiene products of the invention, a dentifrice would be made by preparing an effective amount of the Magnolia Bark Extract in combination with certain surface active agent in a conventional powder or paste carrier, the carrier being comprised of ingredients including a hydrophilic base, emulsifiers, flavoring agents, fragrance agents, and preservatives, in conventional proportions. Such a dentifrice may include effective amounts of abrasive components for mechanical disruption/removal of tartar and/or fluoride. In the solid oral hygiene products, the amount of the active ingredient (MBE and surface active agent) will generally be between about 0.5% and about 5% by dry weight.

Oral hygiene products that may be substantially solid in character include for example toothpowder, and a dental tablet. In different embodiments, the oral hygiene products may be pasty in character, such as toothpaste (dental cream) or gel dentifrice.

The carrier of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminum silicate, zirconium silicate, silica, bentonite, and mixtures thereof. Other suitable polishing materials include the particulate thermosetting resins such as melamine-, phenolic, and urea-formaldehydes, and cross-linked polyepoxides and polyesters. Preferred polishing materials include crystalline silica having particle sized of up to about 5 µm, a mean particle size of up to about 1.1 µm, and a surface area of up to about 50,000 $cm^2/g$, silica gel or colloidal silica, and complex amorphous alkali metal aluminosilicate.

Abrasives are also used in some vehicles for oral care. The total abrasive in the compositions described herein is present at a level of from about 6% to about 70%, preferably from about 15% to about 35% when the dentifrice is toothpaste. Higher levels, as high as 95%, may be used if the composition is a toothpowder.

In some aspects, it may be advantageous to use the antimicrobial composition in the form of a gel, foam, or spray. Such a composition would then contain, in addition to Magnolia Bark Extract and surface active agent as described above, 10 to 90%, preferably 20 to 60% of a blowing agent such as dimethyl ether, carbon dioxide, propane, butane or a halohydrocarbon such as a fluorochlorocarbon or a fluorocarbon or 0.1 to 10%, preferably 0.2 to 2% of a thickener (gelation agent) such as cellulose or chemically modified cellulose derivatives such as hydroxypropylcellulose, hydroxyethylcellulose or water-soluble salts of cellulose ethers, biologically engineered polysugars (such as xanthenes), polyvinyl alcohols, copolymers of maleic acid with vinyl monomers, polyacrylic acid or the salts thereof, polyarylamides, or cationic polymers such as flotation aids.

When visually clear gels are employed, a polishing agent of colloidal silica, such as those sold under the trademark SYLOID as Syloid 72 and Syloid 74 or under the trademark SANTOCEL as Santocel 100, alkali meal alumino-silicate complexes are particularly useful since they have refractive indices close to the refractive indices of gelling agent-liquid (including water and/or humectant) systems commonly used in dentifrices. The forms of insoluble sodium metaphosphate known as Madrell's salt and Kurrol's salt are also examples of suitable materials. The insoluble alkali metal metaphosphate is typically employed in powder form of a particle size such that no more than 1% of the material is larger than 37 µm.

The polishing material is generally present in the solid or pasty compositions in weight concentrations of about 10% to about 99%. Preferably, it is present in amounts from about 10% to about 75% in toothpaste, and from about 70%/o to about 99% in toothpowder. In toothpastes, when the polishing material is silicate in nature, it is generally present in amount of about 10-30% by weight, Other polishing materials are typically present in amount of about 30-75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5-30% by weight of water, 0 to about 70% by weight of glycerine and about 20-80% by weight of sorbitol are preferably employed.

In preparing toothpaste or gels, it is necessary to add some thickening material to provide a desirable consistency of the composition, to provide desirable active release characteristics upon use, to provide shelf stability, and to provide stability of the composition. Thickening agents in an amount from about 0.1% to about 15%, preferably from about 2% to about 10%, more preferably from about 4% to about 8%, by weight of the total toothpaste or gel composition, can be used. Higher concentrations can be used for non-abrasive gels and subgingival gels.

Preferred thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

Another preferred class of thickening or gelling agents includes a class of homopolymers of acrylic acid crosslinked with alkyl ether of pentaerythritol or alkyl ether of sucrose, or carbomers. Carbomers are commercially available from B.F. Goodrich as the Carbopol RTM series. Particularly preferred Carbopols include Carbopol 934, 940, 941, 956, and mixtures thereof.

Another example of a suitable thickener is synthetic hectorite, synthetic colloidal magnesium alkali metal silicate complex clay available for example as Laponite (for example CP, SP 2002, D) marketed by Laporte Industries Limited. Laponite D is, approximately by weight, 58.00% $SiO_2$, 25.40% MgO, 3.05% $Na_2O$, 0.98% $Li_2O$, and some water and trace metals.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (for example available as Natrosol), sodium carboxymethyl cellulose, and colloidal silica such as finely ground Syloid (for example 244). Solubilizing agents may also be included such as humectant polyols such as propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

Copolymers of lactide and glycolide monomers, the copolymer having the molecular weight in the range of from about 1,000 to about 120,000 (number average), are useful for delivery of actives into the periodontal pockets or around the periodontal pockets as a "subgingival gel carrier."

In one aspect of the invention, solid oral hygiene products such as toothpaste or dental cream may be manufactured in layers. In that case, the antimicrobial compounds of the invention may be mixed into the ingredients of one or more of the layers, thereby providing for fast release of the active substance. A specific example of a toothpaste includes Magnolia Bark Extract in an amount of between about 0.2% and about 5% by dry weight in combination with surface active agent and with other toothpaste constituents.

In certain preferred forms of the invention the oral hygiene composition may be substantially liquid in character, such as a mouthwash or rinse. Mouthwashes are liquid preparations specifically designed to cleanse and refresh the mouth. Exemplifying liquid oral hygiene products, an oral rinse such as mouthwash may contain an aqueous or aqueous-alcohol liquid carrier, a preservative, and an effective amount of the Magnolia Bark Extract in combination with certain surface active agent, the antimicrobial compound of the invention being generally between about 0.5% up to about 10% by volume, or 0.005 to 2% by weight.

In one embodiment, the oral hygiene product of the invention is a mouthwash, in which the carrier is water. In a mouthwash preparation of this invention, the vehicle may be a water-alcohol mixture desirably including a humectant as described below. The mouthwash composition may also suitably contain a lower alcohol of 1 to 4 carbon atoms. The alcohol is preferably ethanol or alternatively isopropanol. Generally, the weight ratio of water to alcohol is in the range of from about 1:1 to about 20:1. The total amount of water-alcohol mixture in this type of preparation is typically in the range of from about 70 to about 99.9% by weight of the preparation. In a preferred embodiment, the mouthwash composition of the present invention contains no alcohol. Ethanol is normally included in prior art mouthwashes in order to impart bite and freshness to the mouthwash. The alcohol may, in some instances, act to enhance the solubilization of certain flavor oils, and may enhance the cleansing efficacy. However, adequate antibacterial activity can be achieved and the formulation can remain water-clear without the inclusion of the alcohol in the composition.

In order to render the composition more palatable as a mouthwash it may suitably include a flavoring agent and a colorant, in a flavoring or coloring amount, respectively. Suitable flavoring agents include anise oil and peppermint oil, each of which may be present in an amount of about 0.06%, by volume; suitable colorants include Red Dye No. 7 which may be employed in an amount of about 0.001%, by volume.

In the case in which anise oil or peppermint oil are included in the composition it is appropriate to include a dispersing, suspending or emulsifying agent to disperse, suspend or emulsify the oils in the aqueous medium; one suitable agent is a derivative of castor oil and ethylene oxide also described as a polyethylene glycol glycerol hydrogenated castor oil available from BASF under the trademark Cremophor; this agent may be used in an amount of about 0.8%, by volume.

Additional antibacterial agents may be employed in the mouthwashes of this invention. These include phenolic compounds such as □-naphthol, thymol, chlorothymol, amyl-, hexyl-, heptyl- and octylphenol, hexylresorcinol, hexachlorophene, and phenol; quaternary ammonium compounds such as quaternary morpholinium alkyl sulfates, cetylpyridinium chloride, alkyldimethyl benzylammonium chloride, and alkyltrimethyl ammonium halides; and miscellaneous antibacterial compounds such as benzoic acid, formaldehyde, potassium chlorate, tyrothricin, gramicidin, iodine, sodium perborate, and urea peroxide.

Additionally, the oral hygiene products of the present invention may contain humectants, emulsifiers, colorants and preservatives. The incorporation of these agents into the composition is not critical and where a benefit is seen, their incorporation is recommended.

While the manner of mixing the ingredients is not critical, it is preferred to add all the ingredients into water at ambient temperature or a slightly elevated temperature under constant mixing. Filtration may be employed, after complete mixing, to enhance the clarity of the resulting solution. Buffering agents adjust the pH of the final formulation. Generally, the buffering agent should be capable of bringing the pH to a physiologically acceptable level of between about 3.0 and 8.0, more preferably between 6.3 and 6.7. Exemplary buffering agents are an alkali metal or alkaline earth metal salt, and an amine (for example, ammonium) salt of the weak carboxylic acid. The preferred buffering agents are sodium citrate, potassium citrate, and sodium acetate. Preferably, the buffering agent should be present in the composition at a concentration of from about 2.0% to about 5.0% by weight of the total with the most desired level being about 3.5%.

When contemplating the use of the present composition in either inhibiting oral microorganisms or controlling malodor in the mouth, a sufficient amount of the composition is allowed to contact with the tissue of oral cavity or teeth for a period sufficient to reduce the microorganism population in the mouth or the malodor. Normally, a contact time of less than about 15 seconds is sufficient. Prolonged contact time will increase the effects, and it is preferred that the contact time be about 30 seconds.

It is also contemplated that the product may be prepared in suitable liquid form for regular administration as a denture cleaner. A preferred rinse (denture cleaner) comprises up to 5% by volume of Magnolia Bark Extract and surface active agent diluted with purified water.

The antimicrobial compositions of this invention can also be used by placing 1-20 drops directly on a toothbrush or on commercially available toothpaste and used to brush the teeth and gums.

After application of the oral care product, for example by rinsing, brushing, or application of a gel, or the like, it is preferable that the mouth is not rinsed. However, rinsing after use, as for example if used in or with a toothpaste, will not dramatically reduce the effectiveness of the composition.

The antimicrobial compositions of this invention could be impregnated in, or coated on, solid oral hygiene care products including toothpicks, dental cleaner, floss, or fibers of a toothbrush. This could be done, for example, by stirring Magnolia Bark Extract and surface active agent into a warm gum base and then coating the outer surface of the dental cleaner, floss, toothpick, or toothbrush fibers with a gum base. Coating or impregnation can be performed using jelutong, rubber latex, vinylite resins, and the like, desirably with conventional plasticizers or softeners, sugar or other sweeteners or such as glucose, sorbitol and the like. The antimicrobial gum formulas described in Table 11, or the edible film formulations described in Tables 12 and 13, may be used as actives for coating or impregnation of solid oral hygiene care products.

The dental profession is well aware of the value of the mechanical action of toothpicks to clean out food debris and remove dental plaque. Toothpicks alone remove plaque, but do not treat gingivitis or periodontal disease. Coating or impregnating the toothpick with Magnolia Bark Extract and other therapeutic agents facilitates direct absorption of the medicaments by the periodontal tissues as the active material is wiped off the toothpick and onto the interdental spaces and gums. In one embodiment of this invention, a toothpick coated with antimicrobial agents allows self-administration of the agents directly to the periodontal tissues and treatment of the gingivitis and periodontal disease.

In yet another embodiment of the invention, a dental cleaner coated with antimicrobial agents may be used. Suitable materials for the production of the dental cleaner are wood, bamboo and all physiologically acceptable plastics and metal having sufficient bending strength to push the cleaner into the interdental embrasures in spite of resistance. Plastics and metals can be cast to form a thin sheet and, after solidifying, stamped or processed to form round or angular wires. Among other things, supports made of glass- or carbon fiber-reinforced plastics may also be used. The support can be prepared by roughening or specific shaping such that better adhesion of the adhesive can be achieved for flocking. Shaping can further increase the effectiveness and stability of the toothpick if the plastic films or metal foils are, for example, deformed in the manner of a corrugated sheet. The dental cleaner is impregnated or coated with a mixture of water-soluble carrier and Magnolia Bark Extract in combination with surface active agent.

A carrier or binder can be mixed with the Magnolia Bark Extract and other antimicrobial agents which will either speed or slow its passage through the oral tissues and into the bloodstream. The amount of active material in the coating can be varied according to desired end use. For treating gingivitis and periodontal disease the concentration of the antimicrobial agent(s) will vary by weight, the remainder being binder with the exact amount dependent on the binder's properties, and in particular, the solubility of the active material therein.

The antimicrobial agents may be encapsulated by means of microencapsulation techniques into small beads. Suitable encapsulation materials include, but are not limited to, polymeric coatings such as ethyl cellulose and other coating polymers which coat and preserve the active ingredient until released by mechanical action of the toothpick between teeth and by enzymatic action of the saliva in the mouth. Polymeric coatings that are useful in the present invention include: alkyl monoesters of poly(methyl vinyl ether maleic acid), polyvinyl pyrrolidones, acrylaminde/acrylate/butylaminoethyl methacrylate polymers, terpolymers, copolymers, terpolyarnines, and hydroxypropyl cellulose. Alternatively, the toothpick may be impregnated with antimicrobial agents and subsequently coated with a water-soluble cellulose derivative such as methyl cellulose or sodium carboxymethyl cellulose as a binder.

Using dental floss to help remove plaque from the tooth surface is known in the art. Further, it is known in the art to apply substances and medicaments to dental floss. As an illustration, therapeutic dental floss may be developed by mixing Magnolia Bark Extract, sodium lauryl sulfate, saccharine, flavorings, and benzoate in water. Then the dental floss fiber is passed through this solution into a suitable spool and packaged in a water tight closure. The floss should be used in the usual manner.

In one aspect, the invention is directed to the use of chemically impregnated cotton filaments as a dental floss. This dental floss may be prepared by the process in which cotton filaments of a suitable size are passed through a solution containing Magnolia Bark Extract and surface active agent. Optionally, a wetting agent of polyoxyethylated sorbitan monooleate may be added. The dental floss is then dried by passing it through drying oven to remove the moisture.

Coating the impregnated dental floss with paraffin wax is optional. Coating may facilitate the use and stabilizing the floss until used. Dental floss may also be coated with microcrystalline wax, which is a mixture of hydrocarbons. Numerous grades of microcrystalline wax are available commercially. Such grades of wax are typically food grade materials, which are suitable for coating and adhering to dental floss. The flosses of this invention may thus have incorporated thereon, for instance below, above or within (including encapsulated) their microcrystalline wax coatings, the antimicrobial agents of this invention.

Exemplifying aerosol-based oral hygiene products, another product in which an effective amount of the Magnolia Bark Extract in combination with surface active agent may find use is a throat spray. The spray is used to treat a sore throat by reducing or eliminating the amount of deleterious bacteria to throat tissues.

The antimicrobial composition including Magnolia Bark Extract and a surface active agent can also be applied directly, or with a suitable carrier, to wounds in or around the mouth, including lacerations, incisions, and surgical incisions, to provide antiseptic treatment and the promotion of healing. Other active ingredients or medicaments may be added for various purposes. In the oral care product, the medicament or active will preferably include a base/emulsifier system which leads to the desired concentration of the medicament in the saliva.

Softeners and emulsifiers may include tallow, hydrogenated tallow, hydrogenated and partially hydrogenated vegetable oils, cocoa butter, glycerol monostearate, glycerol triacetate, lecithin, mono and triglycerides, acetylated monoglycerides, fatty acids (for example stearic, palmitic, oleic and linoleic acids), and combinations thereof.

Various other materials may be incorporated in the oral preparations of this invention such as whitening agents, preservatives, silicones, chlorophyll compounds and/or ammoniated material such as urea, diammonium phosphate, and mixtures thereof. Colorants and whiteners may include FD&C dyes and lakes, fruit and vegetable extracts, titanium dioxide, and combinations thereof. These adjuvants, where present, are incorporated in the preparations in amounts which do not substantially adversely affect the properties and characteristics desired.

Any suitable flavoring or sweetening material may also be employed. Examples of suitable flavoring constituents are flavoring oils, for example oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavor and sweetening agents may each or together comprise from about 0.1% to about 5% of the preparation.

High intensity artificial sweeteners can also be used, alone or in combination, with the above. Preferred sweeteners include, but are not limited to, sucralose, aspartame, NAPM derivatives such as neotame, salts of acesulfame, alitame, saccharin and its salts, cyclamic acid and its salts, glycyrrhizinate, stevia, dihydrochalcones, thaumatin, monellin, and the like, alone or in combination. In order to provide longer lasting sweetness and flavor perception, it may be desirable to encapsulate or otherwise control the release of at least a portion of the artificial sweetener. Techniques such as wet granulation, wax granulation, spray drying, spray chilling, fluid bed coating, coacervation, and fiber extension may be used to achieve the desired release characteristics.

In manufacturing the oral care product including the active agent or ingredient, the active agent or medicament is added, preferably, early on in the mix. The smaller the amount of active ingredient used, the more necessary it becomes to preblend that particular ingredient to assume uniform distribution throughout the batch of gum. Whether a preblend is used or not, the active agent or medicament should be added within the first five minutes of mixing. For faster release, the active agent may be added late in the process.

Optionally, the oral care product of the present invention may include additional breath freshening, antimicrobial, or oral health ingredients, such as food-acceptable metallic salts selected from zinc and copper salts of gluconic acid, zinc and copper salts of lactic acid, zinc and copper salts of acetic acid, zinc and copper salts of citric acid and combinations thereof. Further, antimicrobial essential oils and flavor components such as peppermint, methyl salicylate, thymol, eucalyptol, cinnamic aldehyde, polyphosphate, pyrophosphate and combinations thereof may be added to the oral care product. Dental health ingredients, such as fluoride salts, phosphate salts, proteolytic enzymes, lipids, antimicrobials, calcium, electrolytes, protein additives, dental abrasives and combinations thereof may also be added to the oral care composition.

According to another embodiment of the present invention, a method is provided of treating a subject with an oral hygiene product. The method is based on administering an antimicrobial composition to the subject, the composition including Magnolia Bark Extract and a surface active agent in an appropriate ratio.

In the preferred practice of this invention an oral hygiene product according to this invention such as mouthwash or dentifrice containing the composition of the present invention is preferably applied regularly to the gums and teeth, such as every day or every second or third day or preferably from 1 to 3 times daily, for at least 2 weeks up to 8 weeks or more up to a lifetime. In some aspects, topical administration of the compounds of the invention is preferred.

In some aspects, organic surface-active agents may be used in the compositions of the present invention to achieve increased antimicrobial action, assist in achieving thorough and complete dispersion of the active agent throughout the oral cavity, and render the instant compositions more cosmetically acceptable. The organic surface-active material is preferably anionic, nonionic or ampholytic in nature and preferably does not interact with the active agent. It is preferred to employ as the surface-active agent a detersive material which imparts to the composition detersive and foaming properties.

Suitable examples of anionic surface active agents are water-soluble salts of higher fatty acid monoglyceride monosulfates, such as the sodium salt of the monosulfated monoglyceride of hydrogenated coconut oil fatty acids, higher alkyl sulfates such as sodium lauryl sulfite, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral hygiene products of the present invention is particularly advantageous since these materials exhibit a prolonged marked effect in the inhibition of acid formation in the oral cavity due to carbohydrates breakdown in addition to exerting some reduction in the solubility of tooth enamel in acid solutions.

Examples of water-soluble nonionic surface active agents suitable for use are condensation products of ethylene oxide with various reactive hydrogen-containing compounds reactive therewith having long hydrophobic chains (for example aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (for example sorbitan monostearate) and polypropyleneoxide (for example pluronic materials). It is of paramount importance that these surface active agents do not inhibit the antimicrobial action of the compounds of this invention.

All the above-mentioned combinations of different types of compositions or formulation techniques and methods of use apply, whenever relevant, to the composition and method of the invention. It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed is:

1. An antimicrobial oral hygiene product comprising:
   (a) a vehicle for oral delivery;
   (b) a water soluble component; and
   (c) an effective amount of an antimicrobial agent comprising a synergistic ratio of a Magnolia bark extract and sodium lauryl sulfate, wherein the synergistic ratio is at least about 1 part Magnolia bark extract to 1 part sodium lauryl sulfate.

2. The oral hygiene product of claim 1 wherein the sodium lauryl sulfate is present in the oral hygiene product in an amount from about 0.001% to about 2%.

3. The oral hygiene product of claim 1 wherein the synergistic ratio ranges from about 1 part Magnolia bark extract to 1 part sodium lauryl sulfate up to about 4 parts Magnolia bark extract to 1 part sodium lauryl sulfate.

4. The oral hygiene product of claim 1 wherein the synergistic ratio of Magnolia bark extract to sodium lauryl sulfate is about 2 parts Magnolia bark extract to 1 part sodium lauryl sulfate.

5. The oral hygiene product of claim 1 wherein the sodium lauryl sulfate is present in the oral hygiene product in an amount from about 0.001% to about 1%.

6. The oral hygiene product of claim 1, which comprises a mouthwash.

7. The oral hygiene product of claim 1, which comprises a toothpaste or a gel.

8. The oral hygiene product of claim 1, which comprises an oral spray.

9. The oral hygiene product of claim 1, which comprises dental floss.

10. The oral hygiene product of claim 1, which comprises a dentifrice or a dental cleaner.

11. A method of oral cleansing comprising orally administering to a subject in need thereof an oral hygiene product, wherein the oral hygiene product comprises:
    (a) a vehicle for oral delivery;
    (b) a water soluble component; and
    (c) an effective amount of an antimicrobial agent comprising a synergistic ratio of a Magnolia bark extract and a sodium lauryl sulfate, wherein the synergistic ratio is at least about 1 part Magnolia bark extract to 1 part sodium lauryl sulfate.

* * * * *